(12) United States Patent
Pedros et al.

(10) Patent No.: US 8,206,415 B2
(45) Date of Patent: *Jun. 26, 2012

(54) ARTERIAL HOLE CLOSURE APPARATUS (75) Inventors: Roberto Pedros, Seymour, CT (US);
Keith Ratcliff, Newtown, CT (US);
John C. Robertson, Chesire, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 569 days.

This patent is subject to a terminal disclaimer.

(21) Appl. No.: 10/755,428

(22) Filed: Jan. 12, 2004

(65) Prior Publication Data
US 2004/0260339 A1  Dec. 23, 2004

Related U.S. Application Data (63) Continuation of application No. 09/883,427, filed on Jun. 18, 2001, now Pat. No. 6,676,685, which is a continuation of application No. 09/503,510, filed on Feb. 14, 2000, now Pat. No. 6,248,124.

(60) Provisional application No. 60/121,114, filed on Feb. 22, 1999.

(51) Int. Cl.
*A61B 17/08* (2006.01)
*A61D 1/00* (2006.01)

(52) U.S. Cl. .................................................. 606/213

(58) Field of Classification Search .......... 606/213–221, 606/50–52, 139–150, 205–211, 151–158, 606/159; 607/96–99, 115, 128; 227/175.1; 623/23.72; 600/564, 565
See application file for complete search history.

(56) References Cited

U.S. PATENT DOCUMENTS

| | | | | |
|---|---|---|---|---|
| 3,364,933 A | * | 1/1968 | Leopold | 606/207 |
| 4,655,219 A | * | 4/1987 | Petruzzi | 606/206 |
| 5,290,299 A | * | 3/1994 | Fain et al. | 606/142 |
| 5,318,589 A | | 6/1994 | Lichtman | |
| 5,383,880 A | | 1/1995 | Hooven | |
| 5,403,326 A | * | 4/1995 | Harrison et al. | 606/139 |
| 5,456,400 A | * | 10/1995 | Shichman et al. | 227/176.1 |
| 5,507,744 A | | 4/1996 | Tay et al. | |
| 5,573,540 A | * | 11/1996 | Yoon | 606/139 |
| 5,647,115 A | | 7/1997 | Slater et al. | |
| 5,718,709 A | | 2/1998 | Considine et al. | |
| 5,762,609 A | | 6/1998 | Benaron et al. | |
| 5,762,613 A | * | 6/1998 | Sutton et al. | 600/564 |
| 5,827,296 A | | 10/1998 | Morris et al. | |
| 5,836,905 A | | 11/1998 | Lemelson et al. | |
| 5,836,945 A | | 11/1998 | Perkins et al. | |
| 5,910,155 A | * | 6/1999 | Ratcliff et al. | 606/213 |
| 5,916,233 A | | 6/1999 | Chin | |
| 5,928,266 A | | 7/1999 | Kontos | |
| 5,938,660 A | | 8/1999 | Swartz et al. | |

(Continued)

*Primary Examiner* — Melanie Tyson (57) ABSTRACT

A vascular closure device used in closing openings in vessel walls while permitting post-operative flow through the vessel includes a housing, at least two tissue engaging members, and at least two jaw members. The tissue engaging members engage tissue portions on opposite sides of the vessel opening and move tissue to a desired, predetermined position. The jaw members are adapted, in an open position, for positioning about the tissue portions in the predetermined position, and in a closed position, to at least partially draw the tissue together to an at least partially approximated condition. An attachment member is associated with at least one of the jaw members and arranged to contact the tissue. In one embodiment, the attachment member is adapted for connection to an energy source whereby energy is transmitted through the attachment member to thermally fuse the tissue engaged by the jaw members to substantially close the opening.

9 Claims, 5 Drawing Sheets

U.S. PATENT DOCUMENTS

| | | |
|---|---|---|
| 5,954,731 A | 9/1999 | Yoon |
| 5,964,782 A | 10/1999 | Lafontaine et al. |
| 6,004,335 A | 12/1999 | Vaitekunas et al. |
| 6,010,500 A | 1/2000 | Sherman et al. |
| 6,033,427 A * | 3/2000 | Lee ................................ 606/213 |
| 6,063,085 A * | 5/2000 | Tay et al. ......................... 606/50 |
| 6,099,550 A | 8/2000 | Yoon |
| 6,165,183 A * | 12/2000 | Kuehn et al. ................... 606/139 |
| 6,248,124 B1 * | 6/2001 | Pedros et al. ................... 606/213 |
| 6,676,685 B2 * | 1/2004 | Pedros et al. ................... 606/213 |
| 7,252,666 B2 * | 8/2007 | Dycus ............................. 606/51 |

* cited by examiner

ARTERIAL HOLE CLOSURE APPARATUS

This application is a continuation application of application Ser. No. 09/883,427, filed Jun. 18, 2001, now U.S. Pat. No. 6,676,685, which is a continuation application of application Ser. No. 09/503,510, filed Feb. 14, 2000, now U.S. Pat. No. 6,248,124, which claims priority to provisional application 60/121,114, filed Feb. 22, 1999, now expired. The contents of the '427 application, '510 application and '114 provisional application are each incorporated in their entireties by reference.

BACKGROUND

1. Technical Field

The present disclosure relates to an arterial closure device used following a coronary catheterization procedure for closing an arterial access opening formed through the arterial wall while permitting post operative blood flow through the artery.

2. Background of the Related Art

When performing a catheterization procedure such as, for example, an angiography or angioplasty, a sharpened hollow needle is first percutaneously introduced into the vascular system. A guide wire is then inserted through the hollow needle and into the lumen of a selected blood vessel. Subsequently, the needle is removed and a dilator and/or introducer is fed into the vessel along the guide wire. The guide wire is then removed and a suitable catheter is fed through the lumen of the introducer and advanced through the vascular system until the working end thereof is positioned at the operating site. At the conclusion of the catheterization procedure, the catheter is withdrawn, followed by removal of the dilator and/or introducer.

At this point in the procedure, the vessel puncture must be sealed to stem the flow of blood therethrough. Generally, this procedure is extremely difficult due to the nature of the vessel tissue and to the presence of a blood thinning agent which is typically administered prior to the catheterization. A common method of closing the wound is to maintain external pressure over the vessel until the puncture naturally seals. This method of puncture closure typically takes about thirty minutes, with the length of time usually being greater if the patient is hypertensive or anti-coagulated. When hand pressure is utilized, it can be uncomfortable for the patient and can use costly professional time on the part of the hospital staff. Other pressure application techniques, such as pressure bandages, sandbags or clamps, have been employed, but these techniques also require the patient to remain motionless for an extended period of time and the patient must be closely monitored to ensure the effectiveness.

Other devices have been disclosed that plug or otherwise provide an obstruction in the area of the puncture. See, for example, U.S. Pat. Nos. 4,852,568 and 4,890,612, wherein a collagen plug is disposed in the blood vessel opening. When the plug is exposed to body fluids, it swells to create a block for the wound in the vessel wall. A potential problem of plugs introduced into the vessel is that plug particles may break off and float downstream to the point where they may lodge in a smaller vessel, causing an infarct to occur. Collagen material also acts as a nidus for platelet aggregation and, therefore, can cause intraluminal deposition of a hemostatic agent, thereby creating the possibility of a thrombosis at the puncture site. Other plug-like devices are disclosed, for example, in U.S. Pat. Nos. 5,342,393; 5,370,660; and 5,411,520.

U.S. Pat. Nos. 5,417,699 and 5,527,322 each to Klein et al. discloses a suture applying device for the percutaneous suturing of a vascular puncture site. These devices include a shaft which carries a pair of needles at its distal end. The needles are joined by a length of suture. The shaft is used to both introduce the needles within the lumen of the vessel and to draw the needle back through the vessel wall leaving a loop of suture behind to close the puncture site.

U.S. Pat. No. 5,810,810 to Tay et al. discloses an apparatus for closing and sealing a vascular puncture utilizing heat to thermally fuse the vascular tissue. The Tay '810 device includes a vessel balloon occluder which is introduced within the lumen of the vessel to occlude the opening and a forceps which are intended to grasp the vascular tissue surrounding the opening. The forceps serve as electrodes and are energized by radiofrequency energy to thermally fuse the tissue grasped therebetween.

SUMMARY

Accordingly, the present invention is directed to an arterial closure device used following coronary catheterization procedures to close arterial access openings through the arterial wall while permitting post operative flow through the artery. In the preferred embodiments the apparatus includes a housing having proximal and distal ends, and defining a longitudinal axis, first and second arterial tissue everting members mounted adjacent the distal end of the housing and first and second jaw members mounted adjacent the first and second arterial tissue engaging members. The first and second arterial tissue everting members are dimensioned for at least partial positioning within the arterial access opening in the arterial wall and are deployable in at least a radial outward direction relative to the longitudinal axis of the housing to engage respective opposed arterial tissue portions on opposed sides of the opening and move the arterial tissue portions to an everted condition thereof. The first and second jaw members are adapted for relative movement between an open position to facilitate positioning about the arterial tissue portions in the everted condition and a closed position to at least partially draw the arterial tissue portions together to an at least partial approximated condition. An electrode is associated with at least one of the first and second jaw members and arranged to contact the respective arterial tissue portions. The electrode is adapted to be connected to a radiofrequency energy source whereby energy is transmitted through the electrode to thermally fuse the arterial tissue positions between the first and second jaw members to substantially close the opening. Preferably, an electrode is associated with each of the first and second jaw members. Each electrode may be configured as a bipolar electrode.

Each arterial tissue everting member includes a distal memory portion comprising a shape memory material, the distal memory portion being adapted to assume a normal unstressed condition upon deployment to engage and move the arterial tissue portions to the everted condition. The normal unstressed condition of each arterial tissue everting member may be a general hook-shaped configuration. Preferably, the distal memory portions of the tissue everting members define general hook-shaped configurations in diametrical opposed relation and extending in radial opposite directions.

A manually operable deployment member may be operatively connected to the arterial tissue everting members, and movable to deploy the tissue everting members. An actuator is operatively connected to the first and second jaw members with the actuator movable to cause corresponding movement of the first and second jaw members between the open and closed positions.

The apparatus may include an elongated shaft at least partially disposed within the housing. The elongated shaft has camming structure which cooperates with corresponding camming structure of the first and second jaw members to move the jaw members between the open and closed positions.

BRIEF DESCRIPTION OF THE DRAWINGS

Preferred embodiments of the disclosure are described herein with reference to the drawings wherein.

DETAILED DESCRIPTION OF THE PREFERRED EMBODIMENTS

In general, the object of the apparatus is to close an arterial access opening in an arterial wall following a coronary catheterization procedure, to stem the flow of blood through the opening while permitting post operative blood flow through the artery. In the drawings and in the description which follows, the term "proximal", as is traditional, will refer to that end of the apparatus, or component thereof, which is closer to the operator, while the term "distal" will refer to that end of the apparatus, or component thereof, which is more remote from the operator.

Figure 1:
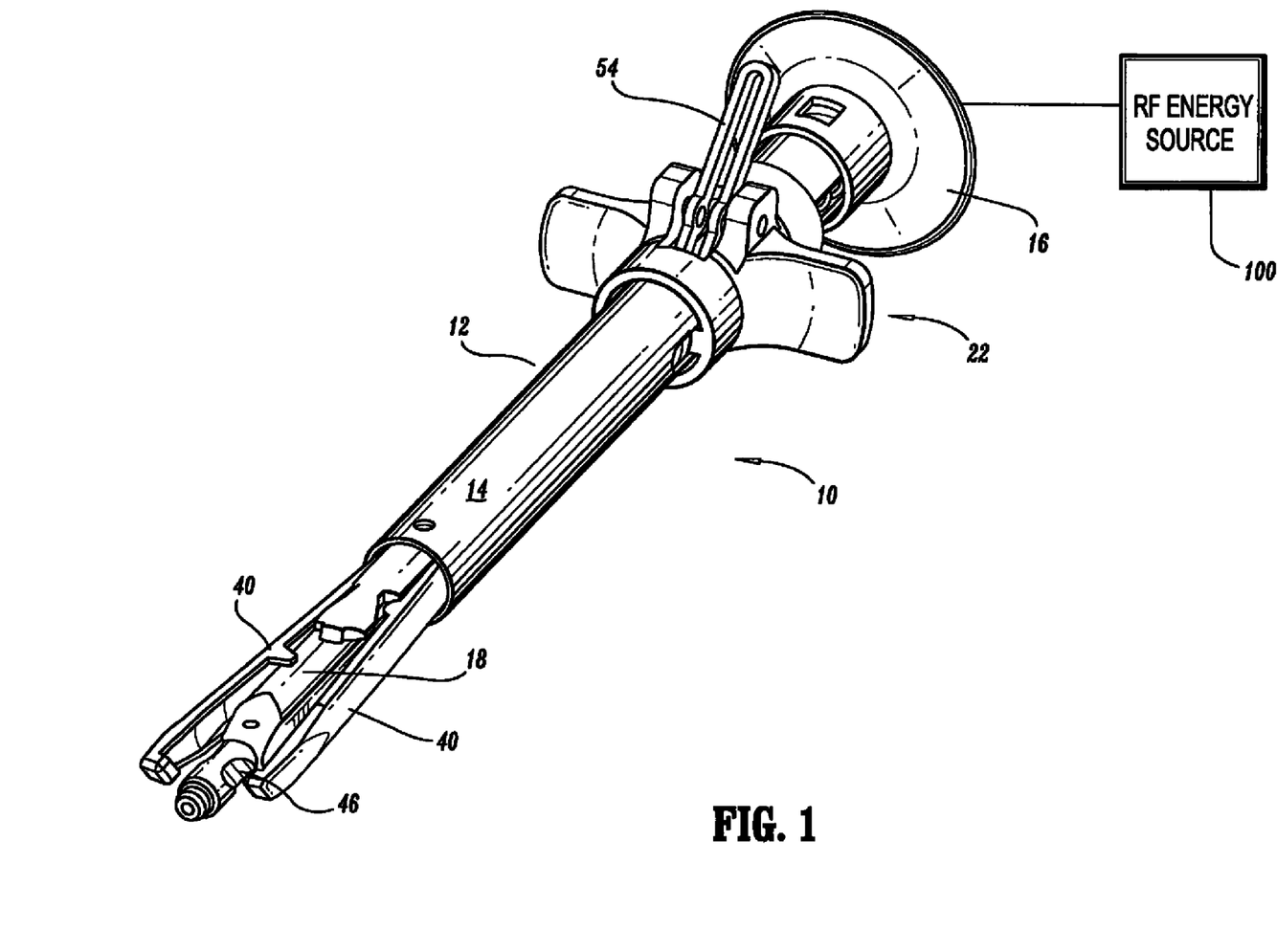
FIG. 1 is a perspective view of the surgical apparatus for facilitating closure of an arterial access opening in the arterial wall in accordance with the principles of the present disclosure.

Referring now in detail wherein like reference numerals identify similar components throughout the several views, FIG. 1 illustrates in perspective the apparatus in accordance with the principles of the present disclosure. Arterial closure apparatus 10 is configured to close an arterial access opening in an arterial wall. In achieving this objective, arterial apparatus 10 has incorporated therein several mechanisms; namely, 1) an arterial tissue everting mechanism which everts the tissue portions on each side of the arterial opening such that the arterial portions are exposed and arranged at a desired orientation; and 2) an arterial tissue approximating mechanism which draws the everted arterial portions to a general closed approximated position and maintains a predetermined degree of pressure on the arterial portions. A thermal treatment mechanism supplies thermal energy across the approximated everted arterial tissue portions for a desired predetermined time and intensity to effectuate complete thermal fusion of the everted arterial portions.

Figure 2:
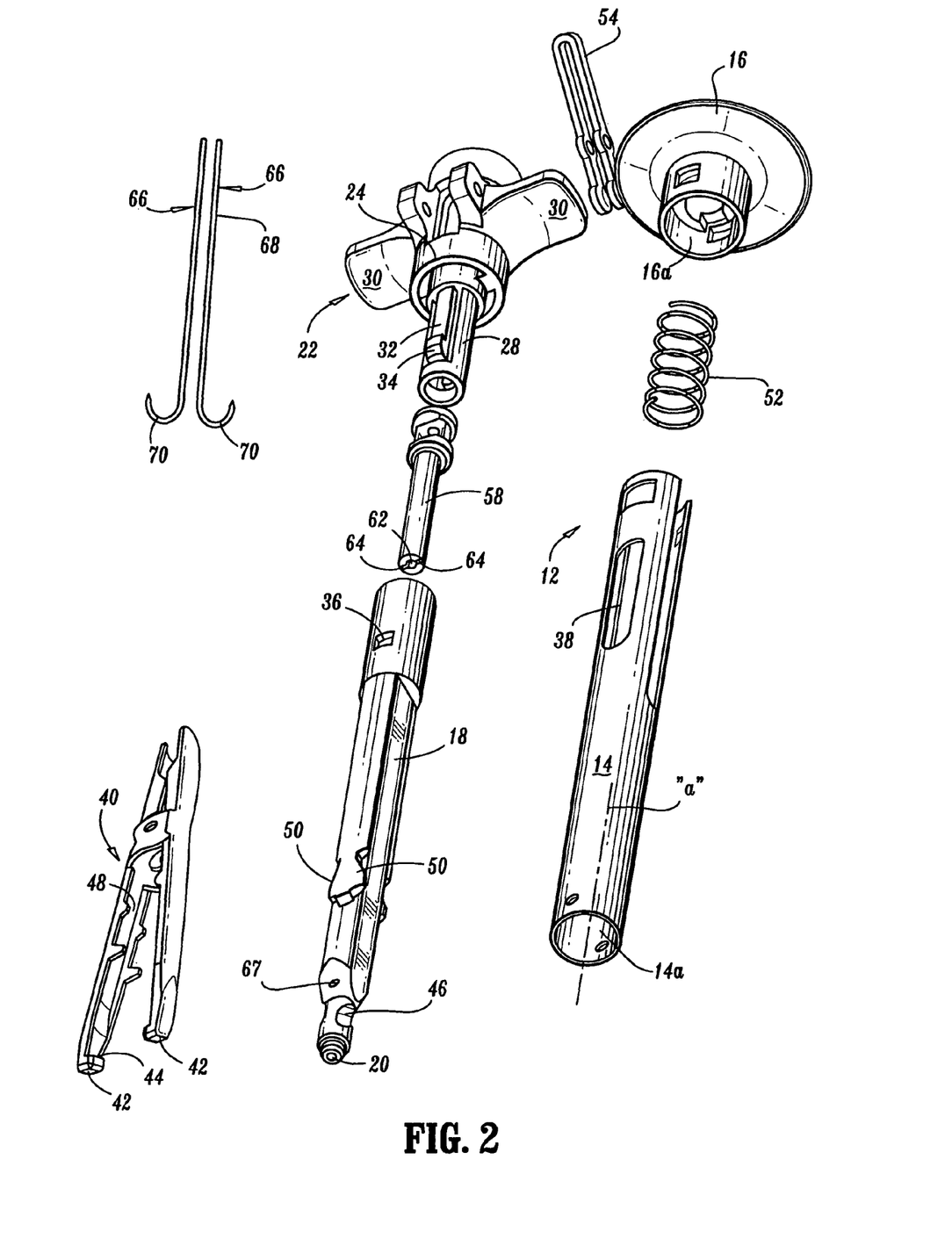
FIG. 2 is a perspective view with parts separated of the apparatus of FIG. 1.
Figure 3:
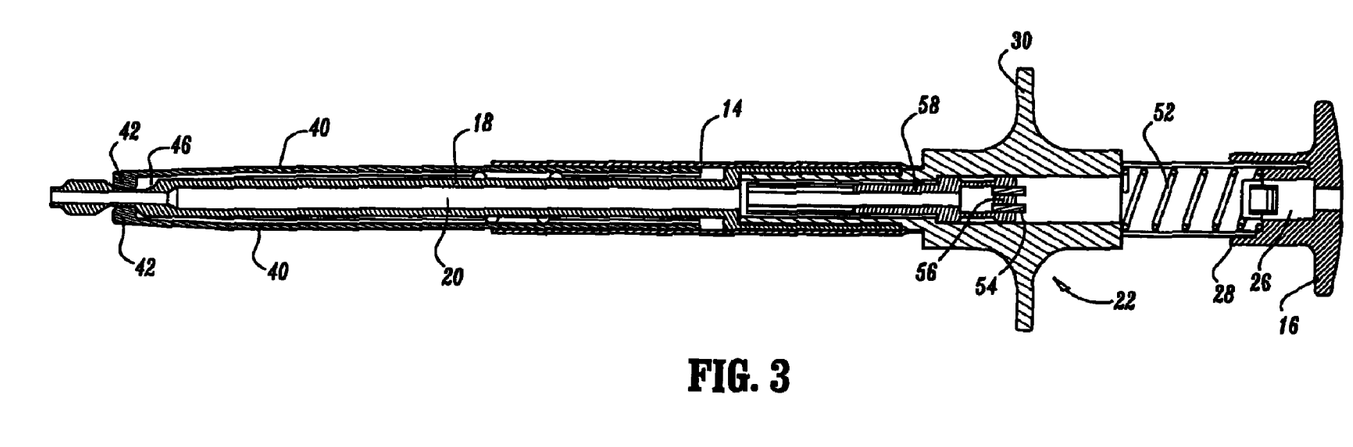
FIGS. 3-4 are side cross-sectional views of the apparatus in an unactuated position.
Figure 4:
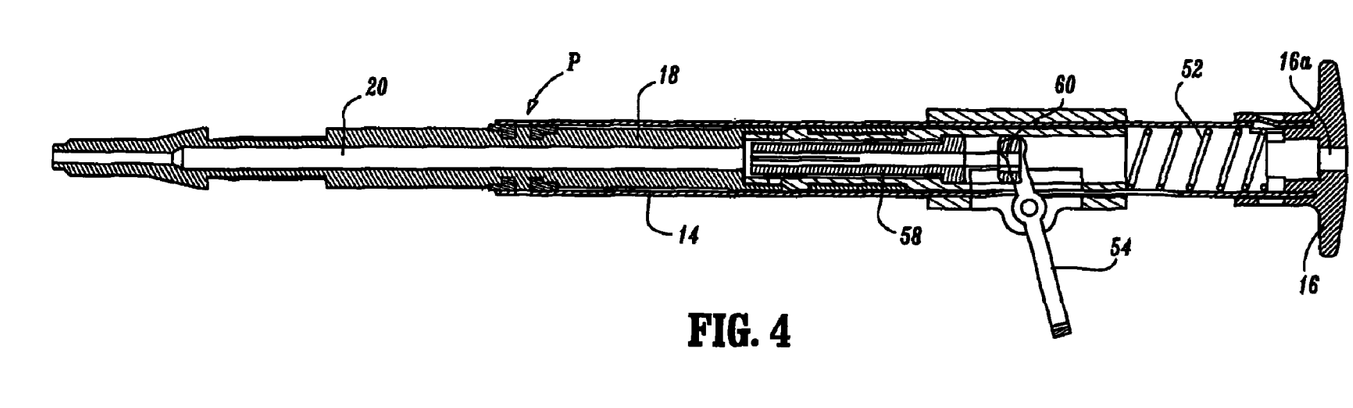

Referring now to FIGS. 2-4, in conjunction with FIG. 1, the components of apparatus 10 will be discussed in detail. Apparatus 10 includes main housing 12 which accommodates the mechanisms discussed above. Main housing 12 includes outer sleeve 14 and circular flange 16 which is fixedly mounted to the proximal end of outer sleeve 14. Outer sleeve 14 defines longitudinal axis "a" and has a longitudinal opening 14a extending completely therethrough. Circular flange 16 also defines longitudinal opening 16a (FIG. 3) in general alignment with the opening of the outer sleeve 14. Circular flange 16 may be fixedly mounted to outer sleeve 14 by any conventional means including adhesives, snap-groove fit, bayonet coupling etc. . . . Outer sleeve 14 and circular flange 16 may be fabricated from any suitable rigid material including stainless steel titanium, or a rigid polymeric material. Housing 12 further includes central elongated shaft 18 disposed within outer sleeve 14 and mounted for relative longitudinal movement therewithin. Central shaft 18 defines a central lumen 20 dimensioned to receive a guide wire. The remaining features and components of housing 12 will be discussed in greater detail below.

With continued reference to FIGS. 2-4, the components of the arterial tissue approximating mechanism will be discussed. The tissue approximating mechanism includes manually operable actuator 22 which is mounted to outer sleeve 14 in a manner to permit relative longitudinal movement of the actuator 22 and the sleeve 14. Actuator 22 includes main portion 24 defining a central lumen 26 and tubular portion 28 extending from the main portion 24. Main portion 24 defines a pair of manually engageable finger grips 30 extending radially outward from the main portion 24. Finger grips 30 are positioned to be engaged by the user's fingers during use while the user's palm engages circular flange 16. Tubular portion 28 of actuator 22 possesses a pair of resilient legs 32 (FIG. 2) extending in a general longitudinal direction. Resilient legs 32 have radially outwardly extending resilient tabs 34 adjacent their distal ends which are received within corresponding slots 36 of elongated shaft 18 in a snap fit manner to connect the two components. With this arrangement, actuator 22 is longitudinally fixed with respect to elongated shaft 18. Tabs 34 of actuator legs 32 are also accommodated within longitudinal slots 38 of outer sleeve 14 to operatively connect these components. Tabs 34 of actuator legs 32 are capable of sliding within slots 38 to thereby provide relative movement between outer sleeve 14 and actuator 22.

Figure 5:
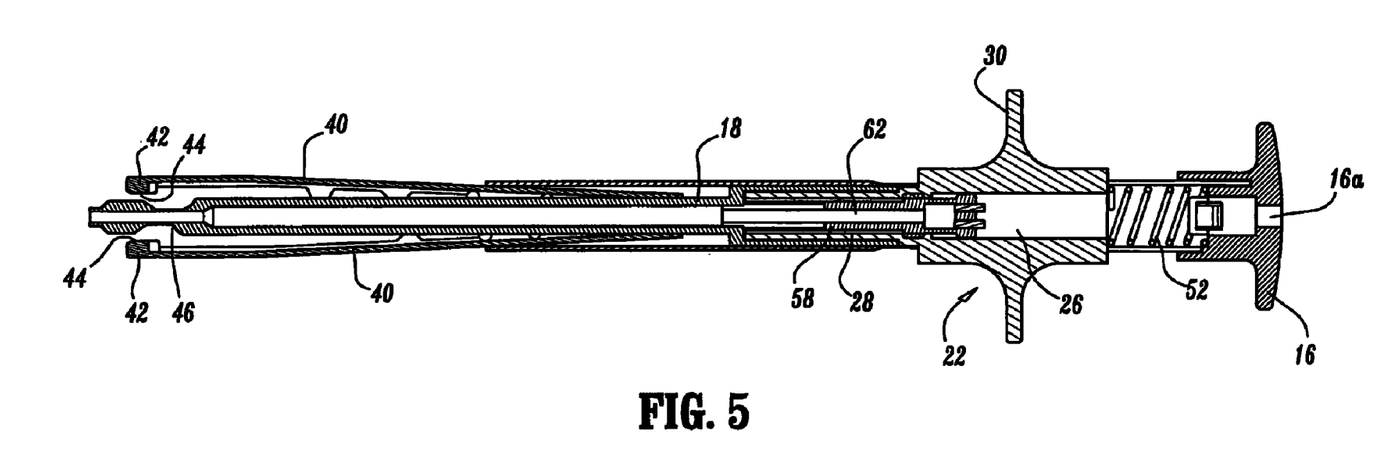
FIGS. 5-6 are side cross-sectional views of the apparatus in an actuated position.
Figure 6:
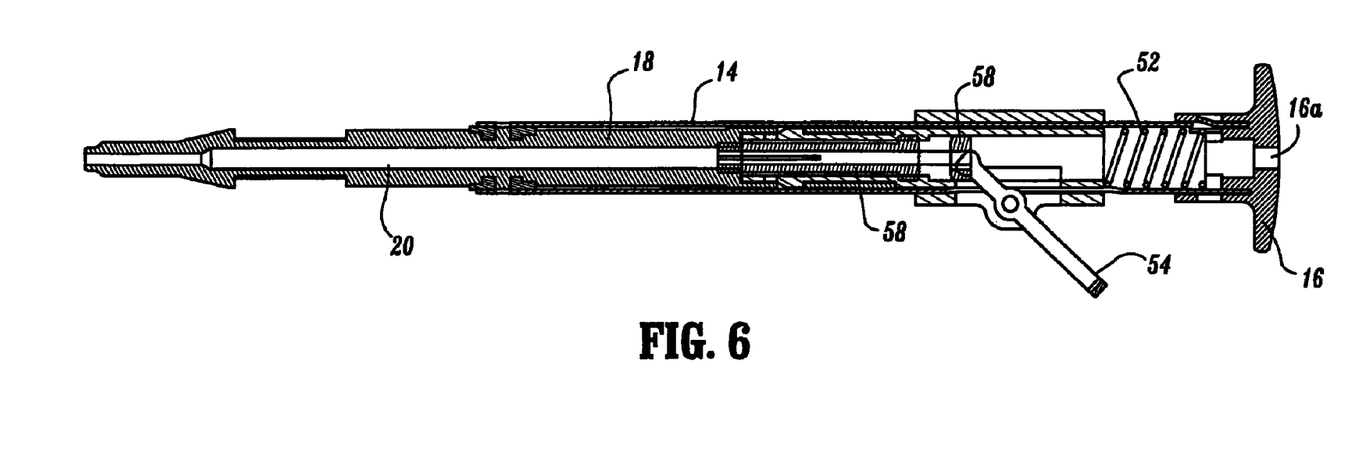

With reference still to FIGS. 2-4, the arterial tissue approximating mechanism further includes a pair of jaw members 40. Jaw members 40 are connected to outer sleeve 14 at location "P" (FIG. 4) through a pivot pin arrangement (not shown) and thus are longitudinally fixed with respect to the sleeve 14. Jaw members 40 are adapted to move or pivot from the closed or approximated position depicted in FIG. 3 to the open position depicted in FIG. 5. Jaw members 40 each define an arterial tissue contacting portion 42 adjacent their respective distal ends. Arterial tissue contacting portion 42 each depend radially inwardly and define a planar tissue contacting surface 44. In the closed position of jaw members 40 depicted in FIG. 3, tissue contacting portions 42 are received within corresponding recesses 46 of elongated shaft 18 to define the reduced profile shown. Jaw members 40 further define first and second interior camming surfaces 48. Camming surfaces 48 engage corresponding camming surfaces 50 of elongated shaft 18 to cause the jaw members 40 to assume the open position depicted in FIG. 5 as will be discussed.

The tissue approximating mechanism is normally biased to the closed position of FIG. 3 by coil spring 52. More particularly, coil spring 52 is in engagement with flange 16 of housing 12 and actuator 22 and serves to normally bias the flange 16 and the actuator 22 in opposite directions, thus biasing outer sleeve 14 and jaw members 40 in the opposite (proximal) direction relative to elongated shaft 18.

With continued reference to FIGS. 2-4, the arterial tissue everter mechanism will be discussed. The arterial tissue everter mechanism includes a manually operative lever 54 pivotally mounted to actuator 22 about pivot pin 56 and drive tube 58 which is operatively connected to operative lever 54 through pin 60. With this arrangement, pivotal movement of lever 54 causes drive tube 58 to longitudinally translate. Drive tube 58 includes central opening 62 which receives guide wire "w" and outer longitudinal slots 64 (FIG. 2) defined in the outer wall of the drive tube 58. With reference to FIG. 2, the tissue everter mechanism further includes a pair of arterial tissue everting members 66. In FIGS. 1 and 3-6, everting members 66 are not shown/visible. Tissue everting members 66 are accommodated within longitudinal slots 64 of drive tube 58 and extend distally with elongated shaft 16 through a pair of longitudinal slots 67 (FIG. 2) defined within the outer wall of the elongated shaft 16. Each tissue everting member 66 is fixed to drive tube 58 by conventional means to thereby longitudinally move with the drive tube 58, but, is capable of sliding within slots 67 of elongated shaft 16. Each everting member 66 defines a generally straight proximal portion 68 and a curved distal portion 70. Tissue everting members 66 are fabricated from a shape memory material such as TinelTM. In the normal unstressed condition of tissue everting members, the distal portions 70 assume the opposed hook or J-shaped configuration shown. In this configuration, the distal portions 70 engage the interior arterial portions to surrounding the vessel opening to evert the tissue portions to a desired orientation. The extreme distal end of each tissue everting member is relatively sharp to facilitate engagement with the vessel portion. In the non-deployed position, tissue everting members 66 are received within longitudinal slots 67 of elongated shaft 18 whereby the curved distal portion is straightened by the biasing affects of the elongated shaft 18.

With reference to FIG. 1, in conjunction with FIG. 3, the thermal treatment energy source 100 is shown in block diagram. The thermal treatment energy source does not form part of the invention as a variety of different generators can be utilized to apply thermal energy to the tissue. Preferably, the energy source includes an RF energy source which is capable of supplying RF energy at a frequency ranging between 10 Khz to 300 GHz. One suitable RF energy source is the WeO Fich LT made by Mentor U&O, Inc. Another suitable power source is the Valley Lab Force FX an Force EZ generator. Other RF generators suitable for this use are envisioned as well such as those enumerated in U.S. Pat. No. 5,810,810. The generator selected may depend on the intended use requirements of the surgeons. Also, energy can be supplied at other frequency ranges other than radiofrequency, as well. The energy source needs to be in electrical contact with jaw member 40. In the illustrated embodiment, this is achieved through conventional leads with electrodes associated with jaw members 40. In one embodiment, the contacting surface 44 of each jaw member 40 functions as the RF electrode and is electrically connected through lead lines (not shown) to the RF power source. Preferably, the RF electrodes are each configured as bipolar electrodes to transmit RF energy therebetween. A monopolar arrangement is envisioned as well. It is also envisioned the jaw members 40 may be conductive with the extreme tissue contacting portion 42 left uninsulated to transmit the thermal energy.

Operation of the Apparatus

The operation of surgical apparatus 10 will now be discussed. Apparatus 10 is used to close an arterial access opening in an arterial wall subsequent to a coronary catheterization procedure while permitting blood flow through the artery. The initial position of apparatus 10 is best depicted in FIGS. 3-4.

Figure 7A:
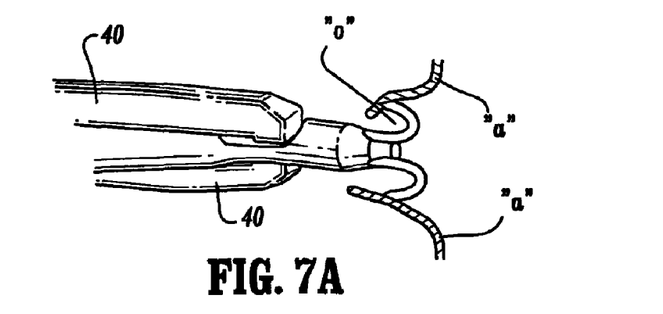
FIGS. 7A-7D are perspective views depicting the sequence of movement of the arterial tissue everters members and the jaw members during movement of the apparatus to the actuated position.

Surgical apparatus 10 is then advanced along a guide wire which had been previously introduced in connection with the angioplasty procedure to access the surgical site. The guide wire is received within the central lumen 20 of elongated shaft 18 and extends proximally within opening 62 of drive tube 58 where it passes through the opening 16a of flange 16. Apparatus 10 is advanced along the guide wire until the distal hub portion is received within the opening of the arterial wall and at least partially disposed within the vessel lumen. Thereafter, lever 54 is pivoted from its initial position of FIG. 3 to its position of FIG. 5 to cause corresponding movement of drive tube 58 and tissue everting members 66 to advance within slots of elongated shaft 18. Upon deployment from elongated shaft 18, distal portions 70 of tissue everting members 66 assume their normal unstressed condition, i.e., the J-shaped configuration shown in FIG. 7A. In this position, the extreme distal ends of the distal hook portion 70 engage the interior arterial wall portions "a" on each side of the opening "o" to essentially draw the wall portions "a" upwardly to an everted position shown in the Figure. It is noted that at this point the surgeon may slightly "pull-back" the apparatus to exaggerate the everted condition of the arterial portions "a" if desired.

Figure 7B:
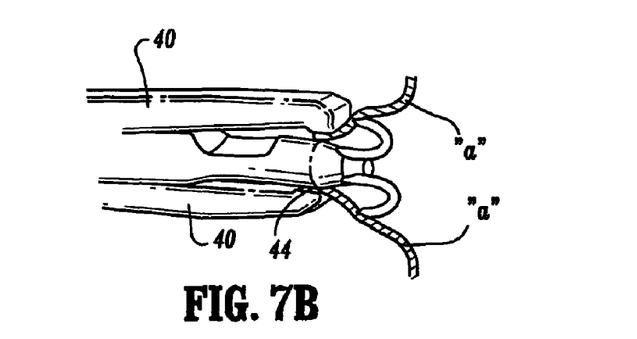
Figure 7C:
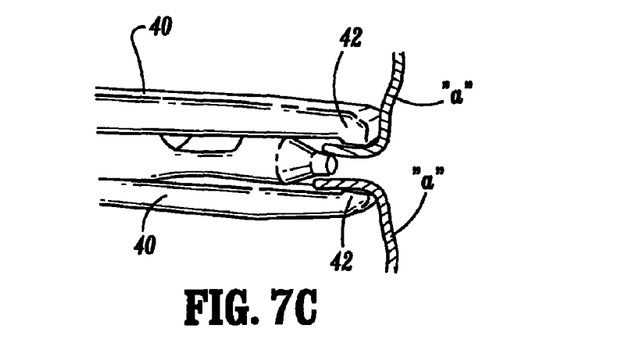
Figure 7D:
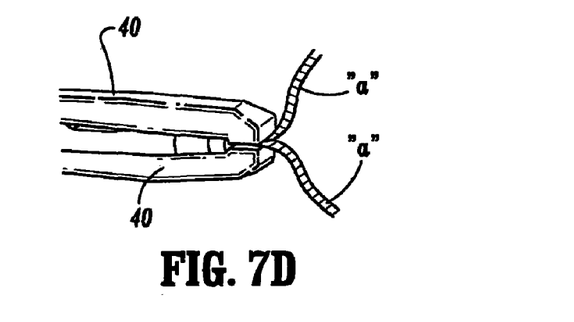

With the arterial portions "a" properly everted, the surgeon thereafter pushes on flange 16 to cause drive sleeve 14 and jaw members 40 to distally move. During such movement, camming surfaces 50 of elongated shaft 18 engage camming surfaces 48 of jaw members 40 to cause the jaw members 40 to pivot outwardly to the open position depicted in FIGS. 5 and 7B. In the open position, the jaw members 40 are positioned about the everted wall portions "a" as depicted in FIG. 7C. Thereafter, jaw members 40 are closed by either releasing actuator 22 or flange 16, or a combination of each movement, to cause the jaw members 40 to close or clamp tightly down on the everted wall portions as shown in FIG. 7D.

With the everted wall portions "a" in their proper everted positions clamped by jaw members 40, the RF energy source is energized to cause current to be emitted through the arterial tissue captured by the jaw members 40. Preferably, the energy is for a sufficient period of time and at an appropriate level to thermally treat and fuse the tissue portions to each other. Once fused, the access opening is closed while blood flow through the artery continues. If desirable, the RF energy source may incorporate various means to detect when treatment has been successfully accomplished or when undesired treatment of neighboring tissue areas occurs. Such means may include temperature sensor means, impedance measurement means, etc. appreciated by one skilled in the art. Other types of feedback mechanism or circuits can optimally be provided as part of the energy source if monitoring of specific parameters is desired by the surgeon. It is noted that the clamping pressure provided by jaw members 40 ensures that the tissue portions are approximated thereby facilitating the fusion process. Upon completion, the apparatus may then be removed from the surgical site along the guide wire.

Although certain embodiments and examples have been used to illustrate and describe the apparatus of the present invention, it is intended that the scope of the invention not be limited to the specific embodiments of the apparatus set forth herein. The scope of the invention is to be defined by the claims which follow.

What is claimed is:

1. An apparatus for substantially closing a vascular opening in a vessel while permitting post operative blood flow through said vessel, which comprises:
   a housing having proximal and distal ends, and defining a longitudinal axis;
   an elongated shaft at least partially positioned within the housing, the elongated shaft defining a longitudinal axis and including a proximal end, a distal end, and a lumen extending between the proximal and distal ends, the lumen being configured and dimensioned to receive a prepositioned guidewire such that the apparatus is movable along the guidewire, the elongated shaft further including recesses disposed in spaced relation to the distal end;

tissue engaging members disposed adjacent the distal end of the housing, the tissue engaging members being adapted for longitudinal movement relative to the elongated shaft to selectively engage vascular tissue positioned adjacent the vascular opening such that the vascular tissue is oriented in a predetermined orientation; and jaw members connected to the housing and positioned adjacent the tissue engaging members, the jaw members being movable between an open position and a closed position independently of movement of the tissue engaging members, wherein, in the open position, the jaw members are configured and dimensioned to seize said vascular tissue when in the predetermined orientation, the jaw members drawing together the vascular tissue during movement from the open position to the closed position, and rendering the vascular tissue in adjacent relation when in the closed position, the jaw members including tissue contacting surfaces the free ends of which depend radially inwardly therefrom towards the longitudinal axis, the tissue contacting surfaces being configured and dimensioned to engage the tissue adjacent the vascular opening, the tissue contacting surfaces being further configured and dimensioned for receipt by the recesses disposed in spaced relation to the distal end of the elongated shaft.

2. The apparatus of claim 1, wherein the tissue engaging members are selectively deployable from the housing such that the tissue engaging members are positioned beyond the distal end of the housing.

3. The apparatus of claim 2, wherein each of the tissue engaging members is composed, in whole or in part, of a shape memory material such that the distal segments of each of the tissue engaging members is adapted to assume a normal unstressed condition upon deployment.

4. The apparatus of claim 2, wherein the tissue engaging members are longitudinally movable relative to the housing between a retracted position and an advanced position.

5. The apparatus of claim 4, wherein the tissue engaging members each include a distal segment arranged in a general hook or J-shaped configuration.

6. The apparatus of claim 5, wherein the distal segments of the tissue engaging members are disposed in general diametrical opposed relation, and generally curve away from the longitudinal axis when the tissue engaging members are in the advanced position.

7. The apparatus of claim 1, wherein the tissue contacting surfaces are planar.

8. The apparatus of claim 1, wherein the jaw members are adapted to longitudinally move from a first longitudinal position corresponding to the closed position to a second longitudinal position corresponding to the open position.

9. An apparatus for substantially closing a vascular opening in a vessel while permitting post operative blood flow through the vessel, which comprises:

a housing having proximal and distal ends, and defining a longitudinal axis;

an elongated shaft at least partially disposed in the housing, the elongated shaft further including recesses formed adjacent the distal end;

tissue engaging members disposed adjacent the distal end of the housing, the tissue engaging members being longitudinally and reciprocally movable relative to the housing between a retracted position and an advanced position in which the tissue engaging members are at least partially exposed from the housing, the tissue engaging members being adapted to cooperate to engage vascular tissue adjacent the vascular opening, the tissue engaging members each having a distal segment arranged in a general hook or J-shaped configuration, the distal segments being disposed in general diametrical opposed relation and generally curving away from the longitudinal axis when the tissue engaging members are in the advanced position;

jaw members connected to the housing and positioned adjacent the tissue engaging members and being movable independently thereof, the jaw members adapted for seizure of the vascular tissue when in an open position of the jaw members, drawing together the vascular tissue during closing of the jaw members, and rendering the vascular tissue in adjacent relation when in a closed position of the jaw members, wherein each of the jaw members includes a tissue contacting surface, the tissue contacting surfaces of the jaw members being further configured and dimensioned for receipt by the recesses formed adjacent the distal end of the elongated shaft;

an energy source connected to the tissue contacting surface to facilitate transmission of energy to the vascular tissue surrounding the vascular opening via the tissue contacting surfaces to thereby thermally fuse the vascular opening, wherein the tissue contacting surfaces are formed from a conductive material such that the tissue contacting surfaces are adapted to transmit energy received from the energy source to the vascular tissue surrounding the vascular opening to thereby thermally fuse the vascular tissue surrounding the vascular opening; and a deployment member connected to the tissue engaging members such that the tissue engaging members are longitudinally movable relative to the housing and between the jaw members, the tissue engaging members being movable in a distal direction to facilitate engagement with the vascular tissue adjacent the vascular opening to orient the vascular tissue in a predetermined orientation, and thereafter, being movable in a proximal direction to draw the vascular tissue between the jaw members to facilitate seizure by the jaw members.

* * * * *